United States Patent
Nelson et al.

(10) Patent No.: US 6,228,880 B1
(45) Date of Patent: May 8, 2001

(54) 4-AMINO-(ETHYLAMINO)-OXINDOLE DOPAMINE AUTORECEPTOR AGONISTS

(75) Inventors: James A. Nelson, Washington Crossing, PA (US); Mira A. Kanzelberger, New York, NY (US); Richard E. Mewshaw, Princeton, NJ (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/287,675

(22) Filed: Apr. 7, 1999

Related U.S. Application Data
(60) Provisional application No. 60/104,588, filed on Apr. 13, 1998.

(51) Int. Cl.$^7$ .......................... A61K 31/404; A61P 25/16; C07D 209/34

(52) U.S. Cl. ............................................ 514/418; 548/486

(58) Field of Search .............................. 514/418; 548/486

(56) References Cited

U.S. PATENT DOCUMENTS
4,835,166 * 5/1989 Kitamura et al. .................... 514/339

FOREIGN PATENT DOCUMENTS
WO9109849 7/1991 (WO).

OTHER PUBLICATIONS
Corsini et al., *Adv. Biochem. Psychopharmacol.*, 16:645–648 (1977).

Tamminga et al., *Science*, 200:567–568 (1978).

Tamminga et al., *Psychiatry*, 43:398–402 (1986).

Lahti et al., *Mol. Pharm.*, 42:432–438 (1993).

* cited by examiner

*Primary Examiner*—Patricia L. Morris
(74) *Attorney, Agent, or Firm*—Joseph M. Mazzarese

(57) ABSTRACT

Compounds having dopaminegic activity are provided, having the formula:

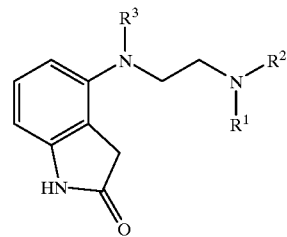

wherein $R^1$ and $R^2$ are each, independently, hydrogen, $C_{1-10}$ alkyl, or $(CH_2)_m R^4$, wherein $R^4$ is phenyl or naphthyl which may be substituted by one or two substituents selected from the group consisting of $C_{1-6}$ alkyl, halogen, $C_{1-6}$ alkoxide and trifluoromethyl and m is 1 to 5; and $R^3$ is hydrogen or $C_{1-6}$ alkyl; or pharmaceutically acceptable salts thereof.

5 Claims, No Drawings

4-AMINO-(ETHYLAMINO)-OXINDOLE DOPAMINE AUTORECEPTOR AGONISTS

CROSS REFERENCE TO RELATED APPLICATIONS

This application claims the benefit of U.S. Provisional Application No. 60/104,588, which was converted from U.S. patent application Ser. No. 09/058,834, filed Apr. 13, 1998, pursuant to a petition filed under 37 C.F.R. 1.53(c)(2)(i) filed May 12, 1998.

FIELD OF THE INVENTION

This invention relates to a series of 4-amino-(ethylamino)-oxindoles having dopaminergic properties. The compounds of the present invention are useful in treating various conditions affected by dopamine agonists, such as Parkinson's disease, Tourette's syndrome, schizophrenia, and alcohol and drug addiction.

BACKGROUND OF THE INVENTION

Efforts to induce antipsychotic activity with dopamine autoreceptor agonists have been successful (e.g., see Dorsini et al., *Adv. Biochem. Psychopharmacol.*, 16:645–648 (1977); Tamminga et al., *Science*, 200:567–568 (1975); and Tamminga et al., *Psychiatry* 398–402 (1986). A method for determining intrinsic activity at the dopamine $D_2$ receptor was recently reported by Lahti et al., *Mol. Pharm.* 42:432–438 (1993). Intrinsic activity is predicted using the ratio of the "low-affinity agonist" (i.e., LowAg) state of the receptor and the "high-affinity agonist" (i.e., HighAg) state of the receptor, i.e. LowAg/HighAg. These ratios correlate with the agonist, partial agonist, and antagonist activities of a given compound. Such activities characterize the ability of a compound to elicit an antipsychotic effect.

WO 9109849 broadly discloses a series of indole-amine compounds, such as, compounds A and B below, that are disclosed as being useful as reverse transcriptase inhibitors for the treatment of AIDS.

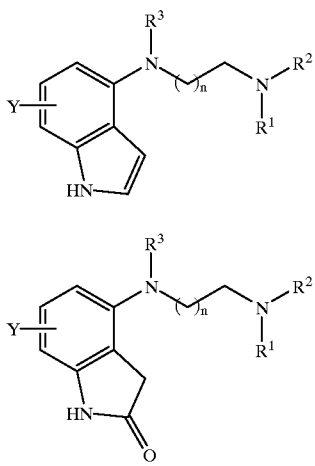

A

B

However, there is no disclosure or suggestion in this reference that such compounds have $D_2$ receptor agonist activity or act to relieve the symptoms of Parkinson's disease, schizophrenia, or other conditions affected by dopamine.

SUMMARY OF THE INVENTION

The compounds of this invention are 4-amino-(ethylamino)-oxindoles represented by Formula I:

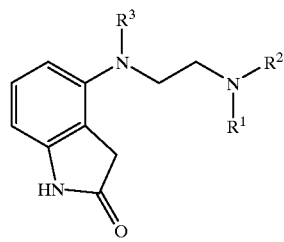

I wherein $R^1$ and $R^2$ are each, independently, hydrogen, $C_{1-10}$ alkyl, or $(CH_2)_m R^4$, wherein $R^4$ is phenyl or naphthyl which may be substituted by one or two substituents selected from the group consisting of $C_{1-6}$ alkyl, halogen, $C_{1-6}$ alkoxide and trifluoromethyl and m is 1 to 5; and $R^3$ is hydrogen or $C_{1-6}$ alkyl; or pharmaceutically acceptable salts thereof.

The compounds of this invention are dopamine agonists having various degrees of intrinsic dopaminergic activity. Some of these compounds are selective autoreceptor agonists, (i.e., partial agonists which activate only autoreceptors versus postsynaptic $D_2$ dopamine receptors). As such, the present compounds provide functional modulation of the dopamine systems of the brain without causing an excessive blockade of the postsynaptic dopamine receptors. Such excessive blockades have been observed to be responsible for the serious side effects frequently exhibited by agents known to be clinically effective for the treatment of schizophrenia. Moreover, the compounds of this invention have a high degree of intrinsic activity and, therefore, they can behave as the natural neurotransmitter, i.e., as a full agonist. As such, they are useful in the treatment of diseases caused by abnormal concentrations of dopamine, such as Parkinson's disease.

DETAILED DESCRIPTION OF THE INVENTION

Preferably, the compounds of the present invention are those of Formula I, wherein:

$R^1$ and $R^2$ are each, independently, $C_{1-10}$ alkyl or $(CH_2)_m R^4$, wherein $R^4$ is phenyl and m is 1; and $R^3$ is hydrogen or $C_{1-6}$ alkyl; or pharmaceutically acceptable salts thereof.

Most preferably, the compounds of the present invention may be selected from the group consisting of:

4-(2-Benzylamino-ethylamino)-1,3-dihydro-indol-2-one dihydrochloride; and

4-[2-(Benzyl-methylamino)-ethylamino]-1,3-dihydro-indol-2-one dihydrochloride.

As used herein, the terms "alkyl" and "alkoxy" refer to either straight or branched chain alllyl and alkoxy groups, respectively. The term "halogen" refers to chlorine, bromine, fluorine and iodine.

The compounds of the present invention may be used in the form of their pharmaceutically acceptable acid addition salts having the utility of the free base. Such salts, preparable by methods well known to those skilled in the art, are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of the present invention are dopamine autoreceptor agonists which modulate the synthesis and release of the neurotranmitter dopamine. They are thus useful for treatment of disorders of the dopaminergic system, such as schzophrenia, Parkinson's disease and Tourette's syndrome. The present compounds are also partial agonists at the postsynaptic dopamine $D_2$ receptor and are thus useful in the treatment of other conditions affected by such agonists, such as alcohol and drug addiction.

The compounds of the present invention may be prepared by any suitable, conventional method which will be recognized by one skilled in the art. However, it is preferred that the present compounds be prepared by the overall sequences depicted in Schemes I and II.

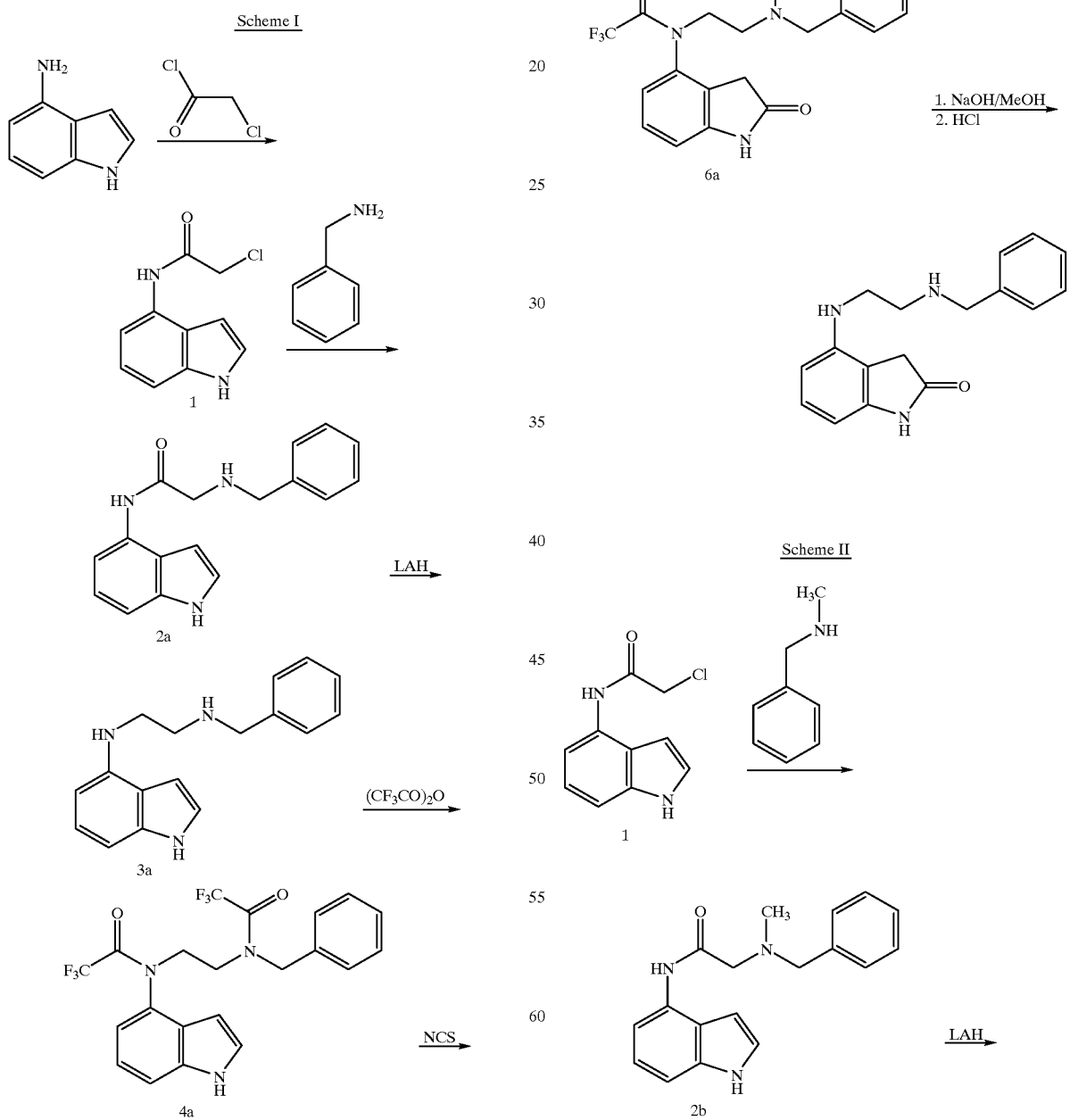

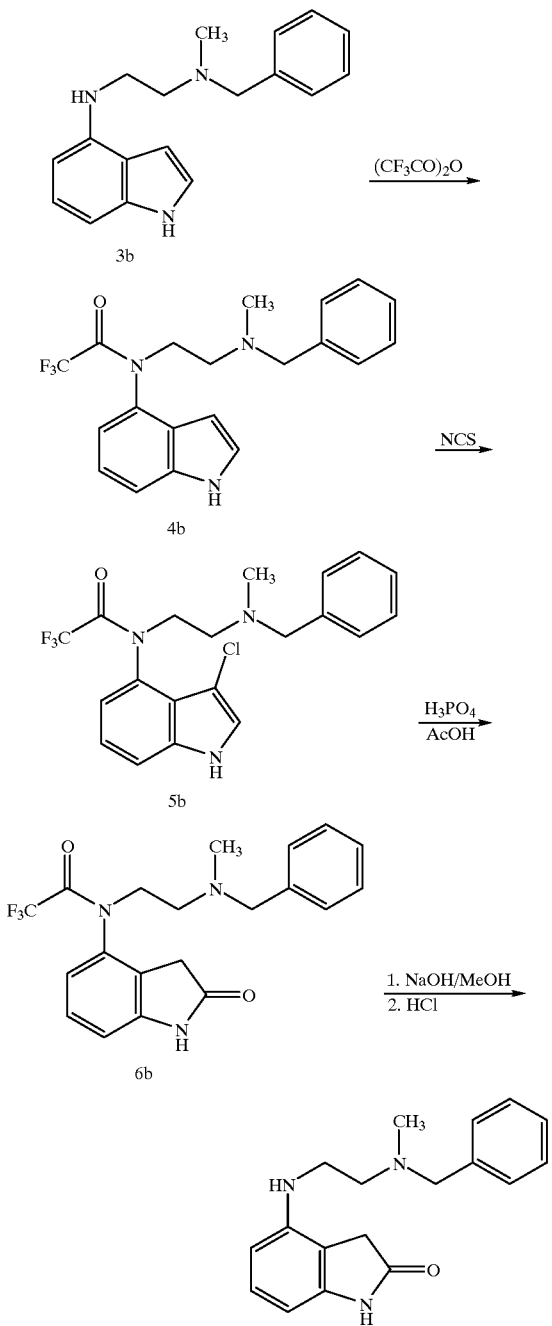

hexane-ethyl acetate afforded the title compound as a white solid (1.17 g, 74.1%), mp 114–116° C.; MS EI m/e 208/210 (M$^+$).

Elemental analysis for $C_{10}H_9ClN_2O$
Calc'd: C, 57.54; H, 4.39; N, 13.31
Found: C, 57.32; H, 4.19; N, 13.19

INTERMEDIATE 2a

2-Benzylamino-N-(1H-indol-4-yl)-acetamide

A solution containing 2-chloro-N-(1H-indol-4-yl)-acetamide (3.0 g, 14.4 mmol), benzylamine (4.76 g, 43.1 mmol) in DMSO (60 mL) was stirred at ambient temperature for 16 hours. The mixture was poured into water (700 mL) and the crude product crystallized as a solid. After filtration, the solids were dissolved in ethyl acetate (600 mL), washed with water (200 mL) and brine (200 mL), dried over anhydrous magnesium sulfate and filtered. Concentration of the ethyl acetate gave the title compound as a white solid, (3.36 g, 83.6%), mp 158–161° C.; MS EI m/e 279 (M$^+$).

Elemental analysis for $C_{17}H_{17}N_3O$
Calc'd: C, 73.10; H, 6.13; N, 15.04
Found: C, 73.19; H, 6.17; N, 14.68

INTERMEDIATE 2b 2-(Benzyl-methyl-amino)-N-(1H-indol-4-yl)-acetamide

The method described for Intermediate 2a was repeated utilizing N-benzylmethylamine. The title compound was obtained as a yellowish-green oil (98.0%); MS EI m/e 293 (M$^+$).

Elemental analysis for $C_{18}H_{19}N_3O$
Calc'd: C, 73.69; H, 6.53; N, 14.32
Found: C, 73.47; H, 6.31; N, 13.97

INTERMEDIATE 3a

N-Benzyl-N'-(1H-indol-4-yl)-ethane-1,2-diamine.quarter hydrate

To a solution of 2-benzylamino-N-(1H-indol-4-yl)-acetamide (3.03 g, 10.8 mmol) in tetrahydrofuran (300 mL) under nitrogen was added slowly 1.0 M lithium aluminum hydride in tetrahydrofuran (54 mL). The mixture was refluxed for 5 hours, cooled, and quenched with aqueous tetrahydrofuran. Sodium hydroxide (1.0 M, 100 mL) was added and the organic layer separated. The aqueous layer was washed with ethyl acetate (2×200 mL). The combined organic layers were washed with water (2×200 mL), brine (200 mL), and dried over anhydrous magnesium sulfate. Filtration followed by concentration of the solvent gave the title compound as a brown oil (2.80 g, 99.0%); MS EI m/e 265 (M$^+$).

Elemental analysis for $C_{17}H_{19}N_3.0.25\ H_2O$
Calc'd: C, 75.66; H, 7.28; N, 15.57
Found: C, 75.40; H, 7.23; N, 15.31

INTERMEDIATE 3b

N-Benzyl-N'-(1H-indol-4-yl)-N-methyl-ethyl-1,2-diamine

The procedure set forth for Intermediate 3a was repeated utilizing 2-(benzyl-methyl-amino)-N-)1H-indol-4yl)-

The present invention will now be illustrated by reference to the following specific, non-limiting examples.

INTERMEDIATE 1

2-Chloro-N-(1H-indol-4-yl)acetamide

To a suspension of 4-aminoindole (1.0 g, 7.57 mmol), triethylamine (1.07 mL, 7.57 mmol) in methylene chloride (50 mL) at 0° C., was added dropwise a solution of chloroacetyl chloride (0.615 mL, 7.57 mmol) in methylene chloride (5 mL). After 30 minutes, the solution was washed with water (2×100 mL) and dried over anhydrous magnesium sulfate. Purification by chromatography over silica gel (60 g, 40% ethyl acetate-hexane) and crystallization form acetamide. The title compound was obtained as an off-white solid (63.9%), mp 73–74° C.; MS EI m/e 279 (M+).

Elemental analysis for $C_{18}H_{21}N_3$
Calc'd: C, 77.38; H, 7.58; N, 15.04
Found: C, 77.24; H, 7.64; N, 15.07

INTERMEDIATE 4a

N-[2-(Benzyl-trifluoroacetyl-amino)-ethyl]-2,2,2-trifluoro-N-(1H-indol-4-yl)-acetamide To a solution of N-benzyl-N'-(1H-indol-4-yl)-ethane-1,2-diamine (1.22 g, 4.60 mmol), triethylamine (2.56 mL, 18.4 mmol) and methylene chloride (40 mL) at 0° C., was added dropwise a solution of trifluoroacetic acid anhydride (1.56 mL, 11.0 mmol) in methylene chloride (5 mL). After 1 hour, the solution was washed with water (2×100 mL), dried over anhydrous magnesium sulfate and filtered. Purification by chromatography over silica gel (60 g, 40% ethyl acetate-hexane) and recrystallization from hexane afforded the title compound as a white solid (1.79 g, 85.7%), mp 174–177° C.; MS EI m/e 459 (M+).

Elemental analysis for $C_{21}H_{17}F_6N_3O_2$
Calc'd: C, 55.15; H, 3.75; N, 9.19
Found: C, 55.19; H, 3.62; N, 9.15

INTERMEDIATE 4b

N-[2-(Benzyl-methyl-amino)-ethyl]-2,2,2-trifluoro-N-(1H-indol-4-yl)-acetamide

The procedure set forth for Intermediate 4a was repeated using N-benzyl-N'-(1H-indol-4-yl)-N-methyl-ethyl-1,2-diamine. The title compound was obtained as an off-white solid (91.2%), mp 105–108° C.; MS EI m/e 375 (M+).

Elemental analysis for $C_{20}H_{20}F_3N_3O$
Calc'd: C, 63.99; H, 5.37; N, 11.19
Found: C, 64.06; H, 5.32; N, 11.22

INTERMEDIATE 5a

N-[2-(Benzyl-trifluoroacetyl-amino)-ethyl]-2,2,2-trifluoro-N-(3-chloro-1H-indol-4-yl)-acetamide A solution containing N-[2-(benzyl-trifluoroacetyl-amino)-ethyl]-2,2,2-trifluoro-N-(3-chloro-1H-indol-4-yl)-acetamide (5.9 g, 12.9 mmol), N-chlorosuccinimide (1.76 g, 12.9 mmol) and acetonitrile (40 mL) was stirred for 16 hours at ambient temperature. The mixture was concentrated and the residue was dissolved in ethyl acetate (50 mL). The organic layer was washed with water (2×100 mL), brine (100 mL), dried over anhydrous magnesium sulfate and filtered. Concentration of the solvent and crystallization from hexane gave the tide compound as a white solid (6.0 g, 95.4%), mp 139–142° C.;; MS EI m/e 491/493 (M+).

Elemental analysis for $C_{21}H_{16}ClF_6N_3O_2$
Calc'd: C, 51.29; H, 3.28; N, 8.54
Found: C, 51.17; H, 3.05; N, 8.43

INTERMEDIATE 5b

N-[2-(Benzyl-methyl-amino)-ethyl]-N-(3-chloro-1H-indol-4-yl)-2,2,2-trifluoro-acetamide The procedure set forth for Intermediate 5a was repeated utilizing N-[2-(benzyl-methyl-amino)-ethyl]-2,2,2-trifluoro-N-(1H-indol4-yl)-acetamide. The title compound was obtained as an off-white solid (72.6%), mp 150–153° C.; MS EI m/e 409/411 (M+).

Elemental analysis for $C_{20}H_{19}ClF_3N_3O$
Calc'd: C, 58.61; H, 4.67; N, 10.25
Found: C, 58.64; H, 4.73; N, 10.19

INTERMEDIATE 6a

N-[2-(Benzyl-trifluoroacetyl-amino)-ethyl]-2,2,2-trifluoro-N-(2-oxo-2,3-dihydro-1H-indol-4-yl)-acetamide To a solution of N-[2-(benzyl-trifluoroacetyl-amino)-ethyl]-2,2,2-trifluoro-N-(3-chloro-1H-indol-4-yl)acetamide (1.4 g, 2.85 mmol) in acetic acid (18 mL) was added a mixture of 85% phosphoric acid (10 mL) and water (3 mL). The reaction was heated at 75–80° C. for 16 hours. The mixture was poured into water (100 mL) and the crude product crystallized as a solid. After filtration, the solids were dissolved in ethyl acetate (100 mL), washed with water (50 mL), saturated sodium bicarbonate solution (50 mL) and brine (20 mL), dried over anhydrous magnesium sulfate and filtered. Purification of the residue by chromatography (silica gel, 40% hexane-ethyl acetate) and crystallization from ether-petroleum ether afforded the title compound as a white solid, (0.31 g, 23.0%), mp 108–111° C.; MS EI m/e 473 (M+).

Elemental analysis for $C_{21}H_{17}F_6N_3O_3$
Calc'd: C, 53.28; H, 3.62; N, 8.88
Found: C, 53.01; H, 3.37; N, 8.92

EXAMPLE 1

4-(2-Benzylamino-ethylamino)-1,3-dihydro-indol-2-one.dihydrochloride.0.1 hydrate To a solution of N-[2-(benzyl-trifluoroacetyl-amino)-ethyl]-2,2,2-trifluoro-N-(2-oxo-2,3-dihydro-1H-indol-4-yl)-acetamide (1.0 g, 2.1 mmol) in tetrahydrofuran (40 mL) was added a mixture of 50% sodium hydroxide (1.0 mL) in methanol (10 mL) at room temperature. After 15 minutes, the mixture is concentrated and the residue was dissolved in ethyl acetate (50 mL). The organic layer was washed with water (2×50 mL), brine (50 mL), dried over anhydrous magnesium sulfate and filtered. Purification by chromatography (silica gel, 7% 2N ammonia in methanol-ethyl acetate) and crystallization from ethyl acetate gave the free base as a light green solid (0.7 g, 87.5%), mp 120–124° C.; MS EI m/e 281 (M+).

Elemental analysis for $C_{17}H_{19}N_3O.0.25\ H_2O$
Calc'd: C, 71.43; H, 6.88; N, 14.70
Found: C, 71.81; H, 6.71; N, 14.73

To a solution of 4-(2-benzylamino-ethylamino)-1,3-dihydro-indol-2-one (0.45 g, 1.6 mmol) in tetrahydrofuran (25 mL) and methanol (20 mL) was added 1 M hydrogen chloride in ether (4.0 mL). Upon concentration of the solvent, the title compound crystallized as a gray solid (0.52 g, 91.2%), mp 184–195° C.; MS EI m/e 281 (M+).

Elemental analysis for $C_{17}H_{19}N_3O.2\ HCl.0.1\ H_2O$
Calc'd: C, 57.34; H, 6.00; N, 11.94
Found: C, 57.00; H, 5.90; N, 11.72

EXAMPLE 2

4-[2-(Benzyl-methyl-amino)-ethylamino]-1,3-dihydro-indol-2-one.dihydrochloride.0.8 hydrate To a solution of N-[2-(benzyl-methyl-amino)-ethyl]-N-(3-chloro-1H-indol-4-yl)-2,2,2-trifluoro-acetamide (5b, 1.75 g, 4.27 mmol) in acetic acid (27 mL) was added a mixture of 70% phosphoric acid (20 mL). The reaction was heated at 75–80° C. for 16 hours. The mixture was poured into water (100 mL) and the crude product crystallized as a solid. After filtration, the solids were dissolved in ethyl acetate (100 mL), washed with water (50 mL), saturated sodium bicarbonate solution (50 mL) and brine (20 mL), dried over anhydrous magnesium sulfate and filtered. Concentration of the ethyl acetate, afforded crude Intermediate 6b as a dark green residue (1.5 g). Without further purification, this material was dissolved in tetrahydrofuran (40 mL), and a mixture of 50% sodium hydroxide (1.0 mL) in methanol (10 mL) was added at room temperature. After 15 minutes, the mixture was concentrated and the residue was dissolved in ethyl acetate (50 mL). The organic layer was washed with water (2×50 mL), brine (50 mL), dried over anhydrous magnesium sulfate and filtered. Purification by chromatography (silica gel, 7% 2N ammonia in methanol-ethyl acetate) and crystallization from ethyl acetate gave the free base as a off white solid (0.48 g, 40.4 %), mp 122–124° C.; MS EI m/e 295 (M+).

Elemental analysis for $C_{18}H_{21}N_3O \cdot 0.25\ H_2O$

Calc'd: C, 72.09; H. 7.23; N, 14.01

Found: C, 72.11; H, 7.16; N, 14.05

The affinity for the dopamine autoreceptor was established by the standard experimental test procedure of Seemen and Schaus, *European Journal of Pharmacology*, 203:105–109 (1991). According to this procedure, homogenized rat striatal brain tissue was incubated with the appropriate concentrations of test compound, filtered and washed and counted in a Betaplate scintillation counter.

High affinity for the dopamine D2 receptor was established by the standard experimental test procedure of Fields, et al., *Brain Res.*, 136:578 (1977) and Yamamura et al., eds., *Neurotransmitter Receptor Binding*, Raven Press, N.Y. (1978). Homogenized limbic brain tissue was incubated with $^3$H-spiroperidol (Spiper.) and the appropriate concentrations of test compound, filtered, washed and shaken with Hydrofluor scintillation cocktail (available from National Diagnostics) and counted in a Packard 460 CD scintillation counter.

The results of the tests with compounds representative of this invention are set forth below.

| Example No. | $IC_{50}$ (nM) $D_2$ Quin. | $IC_{50}$ (nM) $D_2$ Spiper | Ratio |
|---|---|---|---|
| 1 | 13.2 | 892 | 67.7 |

Hence, it can be seen that the compounds of this invention effect the synthesis of the neurotransmitter dopamine and are therefore dopamine antireceptor agonists. Such compounds are useful in the treatment of dopaminergic disorders such as schizophrenia, Parkinson's disease, Tourette's Syndrome, alcohol addiction, cocaine addiction, and addiction to analagous drugs.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be subdivided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

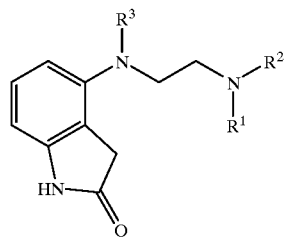

wherein $R^1$ and $R^2$ are each, independently, hydrogen, $C_{1-10}$ alkyl, or $(CH_2)_m R^4$, wherein $R^4$ is phenyl or naphthyl which may be substituted by one or two substituents selected from the group consisting of $C_{1-6}$ alkyl, halogen, $C_{1-6}$ alkoxide and trifluoromethyl and m is 1 to 5; and $R^3$ is hydrogen or $C_{1-6}$ alkyl; or pharmaceutically acceptable salt thereof.

2. A compound according to claim 1, wherein $R^1$ and $R^2$ are each, independently, $C_{1-10}$ alkyl, or $(CH_2)_m R^4$, wherein $R^4$ is phenyl and m is 1; and $R^3$ is hydrogen or $C_{1-6}$ alkyl; or pharmaceutically acceptable salt thereof.

3. A compound according to claim 1 which is 4-(2-Benzylamino-ethylamino)-1,3-dihydro-indol-2-one dihydrochloride.

4. A compound according to claim 1 which is 4-[2-(Benzyl-methylamino)-ethylamino]-1,3-dihydro-indol-2-one dihydrochloride.

5. A pharmaceutical composition comprising an effective amount of a compound of the formula:

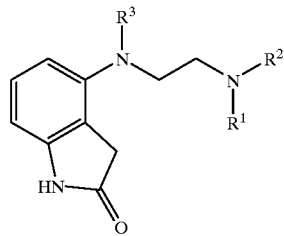

wherein $R^1$ and $R^2$ are each, independently, hydrogen, $C_{1-10}$ alkyl, or $(CH_2)_m R^4$, wherein $R^4$ is phenyl or naphthyl which may be substituted by one or two substituents selected from the group consisting of $C_{1-6}$ alkyl, halogen, $C_{1-6}$ alkoxide and trifluoromethyl and m is 1 to 5; and $R^3$ is hydrogen or $C_{1-6}$ alkyl; or a pharmaceutically acceptable salt thereof.

* * * * *